United States Patent
Weber et al.

(10) Patent No.: US 10,106,838 B2
(45) Date of Patent: Oct. 23, 2018

(54) METHOD AND KIT OF PARTS FOR EXTRACTION OF NUCLEIC ACIDS

(71) Applicant: IFP PRIVATES INSTITUT FUR PRODUKTQUALITAT GMBH, Berlin (DE)

(72) Inventors: Wolfgang Weber, Berlin (DE); Christine Werner, Potsdam (DE)

(73) Assignee: IFP PRIVATES INSTITUT FÜR PRODUKTQUALITÄT GMBH, Berlin (DE)

( * ) Notice: Subject to any disclaimer, the term of this patent is extended or adjusted under 35 U.S.C. 154(b) by 268 days.

(21) Appl. No.: 15/123,655

(22) PCT Filed: Mar. 3, 2015

(86) PCT No.: PCT/EP2015/054341
§ 371 (c)(1),
(2) Date: Sep. 5, 2016

(87) PCT Pub. No.: WO2015/132216
PCT Pub. Date: Sep. 11, 2015

(65) Prior Publication Data
US 2017/0081704 A1 Mar. 23, 2017

(30) Foreign Application Priority Data

Mar. 7, 2014 (DE) .................. 10 2014 103 107
Mar. 7, 2014 (EP) ..................... 14158441

(51) Int. Cl.
*C12Q 1/68* (2018.01)
*C12Q 1/6806* (2018.01)
*C12N 15/10* (2006.01)
*C12Q 1/689* (2018.01)

(52) U.S. Cl.
CPC ....... *C12Q 1/6806* (2013.01); *C12N 15/1003* (2013.01); *C12Q 1/689* (2013.01)

(58) Field of Classification Search
CPC .......................... C12Q 1/6806; C12N 15/1003

USPC .......................... 435/6.1; 536/25.4
See application file for complete search history.

(56) References Cited

U.S. PATENT DOCUMENTS

| 8,357,504 B2 | 1/2013 | Weber et al. |
| 8,785,210 B2 | 7/2014 | Weber |
| 2003/0170664 A1 | 9/2003 | Mori et al. |

FOREIGN PATENT DOCUMENTS

| EP | 0512767 | 11/1992 |
| EP | 2634254 | 9/2013 |
| WO | 2006073472 | 7/2006 |
| WO | 2013101674 | 7/2013 |

OTHER PUBLICATIONS

Neha Jain et al., "Real-time Loop-mediated Isothermal Amplification Assay for Rapid and Sensitive Detection of Anthrax Spores in Spiked Soil and Talcum Powder," 27 World J. Microbiol. Biotechnol. 1407 (2011).
Linda Monaci et al., "Immunochemical and DNA-based Methods in Food Allergen Analysis and Quality Assurance Perspectives," 21 Trends in Food Sci. & Tech. 272 (2010).
Lenka Drabkova, "DNA Extraction From Herbarium Specimens," 1115 Methods in Molecular Biology 69 (Jan. 1, 2014).
Justin O'Grady et al.,"Rapid Real-time PCR Detection of Listeria monocytogenes in Enriched Food Samples Based on the ssrA gene, a Novel Diagnostic Target," 25 Food Microbiology 75 (2008).
Andrew Sails et al., "A Real-time PCR Assay for the Detection of Campylobacter jejuni in Foods After Enrichment culture," 69 Applied and Environmental Microbiology 1383 (2003).

*Primary Examiner* — Jezia Riley
(74) *Attorney, Agent, or Firm* — James C. Lydon

(57) ABSTRACT

Composition, method and kit of parts for a simplified and safe extraction of nucleic acids from biological samples, such as crude and processed food, and subsequent analysis by polymerase chain reaction to the presence of animal material, genetically modified organisms, allergens and pathogens. The method comprises the addition of extracting composition together with hot water for extraction and stabilization of nucleic acids as well as removal of substances interfering with DNA polymerase activity.

13 Claims, 2 Drawing Sheets

METHOD AND KIT OF PARTS FOR EXTRACTION OF NUCLEIC ACIDS

FIELD OF THE INVENTION

The invention relates to a process for the isolation and purification of nucleic acids from food samples for subsequent analysis, notably by PCR, and to a chemical composition and kit for use in the isolation of nucleic acids.

BACKGROUND OF THE INVENTION

Food safety and labelling regulations are increasing with the volume of trade. This also represents a challenging situation for food supply chains. Industrial food processing further enhances the risks of contamination with microorganisms and inadvertent allergens. As consumers and regulatory bodies demand certainty in regard to the products, correct identification and labelling of ingredients is needed, for example, with respect to species in processed mixtures of meat or plant materials. This applies also to biological products such as garments, textiles and furs, e.g. many Western consumers do not wish to wear cat furs due to allergies or ethical reasons.

Isolation and PCR analysis of nucleic acids is a common method for detection and identification of species or undesired organisms. Commonly, the sample of biological material is disrupted mechanically and lysed by chemical treatment, followed by subsequent purification of the isolated nucleic acids. However, the raw and processed samples exhibit very diverse compositions and, accordingly, they require differential treatment and sample processing. It is difficult to know in advance which type of sample processing is needed to obtain enough and sufficiently pure nucleic acids for further PCR analysis.

EP 2 634 254 B1 (QIAGEN GmbH) discloses a method for isolating bacterial DNA from enrichment cultures, in which the sample is mixed with a water-immiscible substance. WO 2013/010674 A1 describes a DNA isolation method using a filtering device containing bentonite for a removal of proteins. The most established method for the isolation of genomic DNA employs the cationic surfactant hexadecyltrimethylammonium bromide (CTAB) for denaturing and removal of proteins (Drábková LZ et al., *DNA extraction from herbarium specimens*, Methods Mol Biol. 2014; 1115:69-84). This method requires the use of an expensive and hazardous chemical and is also laborious and time consuming. The state of the art represents, therefore, a problem.

SUMMARY OF THE INVENTION

The problem is solved by a composition and method as described in claims 1 and 8. Preferred embodiments of the invention are disclosed in the dependent claims 2 to 7 and 9 to 13.

The composition for use in extracting and purifying nucleic acids is made up of a mixture of solids comprising from 10 to 40 percent by weight particles consisting of water-insoluble hydrated magnesium silicate and having a median particle size from 0.8 to 2.5 µm; and from 20 to 70 percent by weight crystalline phosphate buffered saline which is readily water-soluble to produce a solution having a pH from 5.5 to 7.0 at 70 to 95 degrees Celsius. In a preferred embodiment, the composition and mixture of solids has been portioned as a tablet or capsule having a known predefined weight so that it is only necessary to weigh in the amount of sample and not the amount of the purifying and release agent. The composition preferably comprises from 20 to 35 percent by weight of a hydrophilic colloid which is effective to disperse the mixture of solids in water. The particles of hydrated magnesium silicate preferably have a median particles size from 1.0 to 2.0 µm, most preferably from 1.2 to 1.5 µm.

In a preferred embodiment, the present disclosure relates to a tablet or capsule essentially comprising a composition comprising from 10 to 25 percent by weight of water-insoluble hydrated magnesium silicate particles; from 45 to 70 percent by weight phosphate buffered saline, and from 20 to 30 percent by weight of a hydrophilic colloid effective to disperse the mixture of solids in water. The composition may further comprise one or more non-chaotropic cell-lysing agents. The hydrophilic colloid may be selected from one or more of cellulose, carboxy-methyl cellulose, cellulose derivatives, alginate, starch, xantan gum, arabic gum, guar gum or mixtures thereof.

The disclosed standard method of isolating DNA from a diversity of feed and food samples, including beverages, for subsequent PCR analysis, comprises the following steps: (i) obtaining a predefined weight or volume amount of the sample, preferably as small particles, solution or dispersion, and transferring the sample into a vessel; (ii) adding a predefined amount of the mixture of solids as disclosed above, to obtain a weight ratio of solids to sample in the vessel from 1:5 to 5:1; (iii) further adding an amount of water to dissolve the buffer components of the mixture of solids to obtain an aqueous phosphate buffered saline solution having a pH from 5.5 to 7.0 and a salt concentration of 0.6 to 1.2 Mol/L, (iv) obtaining a dispersion of the sample and the mixture of solids in phosphate buffered saline and heating the solution or dispersion up to a temperature from 70 to 95 degrees Celsius for 1 minute to 30 minutes, preferably for about 5 minutes to 20 minutes, to release the nucleic acids from the cellular materials and other water-insoluble components of the sample; (v) separating the water-insoluble components of the sample and of the mixtures of solids from the aqueous phase, preferably by centrifugation or filtration, together with the components adsorbed on the magnesium silicate particles of the mixture of solids; (vi) removal of the aqueous supernatant or filtrate containing soluble nucleic acids, followed by a desalting step to obtain a solution of the sample DNA suitable for PCR analysis. A person skilled in the art will appreciate that one or more steps in this method are interchangeable without departing from the disclosed purification principle.

An another embodiment relates to a kit of parts for extracting and purifying nucleic acids from samples, comprising portioned amounts of the disclosed composition and mixture of solids. The composition, method and kit may be used for isolating and characterizing the type of nucleic acids from raw and/or processed animal and plants materials and processed products thereof. They are in particular suited for isolating nucleic acids characteristic for potential allergens present in cereals and products thereof, chickpea and products thereof, casein, almond and products thereof, cashew and products thereof, peanut and products thereof, hazelnut and products thereof, macadamia and products thereof, mustard and products thereof, soya and products thereof, sesame and products thereof, walnut and products thereof, pistachio and products thereof, lupin and products thereof, celery and products thereof, fish and products thereof, crustaceans and products thereof. They are further suitable for isolating nucleic acids characteristic for genetically modified organisms, pathogens, *Salmonella* spp., *List-*

*eria* spp. *Shigella* spp., *Campylobacter* spp., *Cronobacter*, *Clostridium* spp., *Legionella* spp., *Enterobacteriaceae*, *Escherichia* spp.

In another embodiment the composition, method and kit can be used for the isolation of nucleic acids from fecal samples, preferably human and animal fecal samples.

The composition for extracting and purifying nucleic acids from food samples may comprise from 10 to 40 percent by weight of water-insoluble hydrated magnesium silicate particles; from 20 to 70 percent by weight of a crystalline phosphate buffered saline which is soluble in water effectively producing a solution having a pH from 5.5 to 7.0; and from 20 to 35 percent by weight of a hydrophilic colloid which swells in contact with water and is effective to disperse the mixture of solids in water. The hydrated magnesium silicate used may have a median particle size of 1.2 µm and a density of 2.8 g/cm3. In a preferred embodiment, the mixture of solids may be a tablet or capsule so that the dissolving of the mixture of solids in an aqueous solution may result in 5 to 7 times phosphate buffered saline having a pH 5.5 to 7 at about 70 to about 95 degrees Celsius.

One aspect of the present disclosure relates to a method of purifying genomic DNA from food samples, comprising the steps of i) obtaining a predetermined amount of a food sample; ii) transferring the food sample into a reaction tube; iii) adding the mixture of solids of the present disclosure to the food sample, wherein said mixture of solids comprises phosphate buffered saline which is soluble in water effectively producing a solution having a pH from 5.5 to 7.0; iv) adding a predetermined amount of water; v) mixing the sample and said mixture of solids, wherein the content of the tablet is released producing a solution having a concentration 5 to 7× phosphate buffered saline; vi) heating the reaction tube up to a temperature ranging from 70 to 95 degrees Celsius; and vii) extracting nucleic acids from the food matrix, followed by recovery of the extracted nucleic acids; wherein the food matrix is incubated with the nucleic acid extracting composition in step vi) for a period of time sufficient to extract the nucleic acids.

The disclosure further relates to a method of preparing a nucleic acid extracting composition, comprising the steps of i) providing a particulate solid mixture of from 10 to 40 percent by weight water-insoluble hydrated magnesium silicate particles; and from 20 to 70 percent by weight of crystalline phosphate buffered saline; ii) adding from 20 to 35 percent by weight of a hydrophilic colloid to said particulate mixture; iii) compacting said particulate mixture together with the hydrophilic colloid into a tablet or capsule; and optionally, coating the tablet or capsule with a film.

In another aspect, the disclosure provides a kit of parts for extracting and purifying nucleic acids from food samples, comprising i) a tablet or capsule having the composition according to the present disclosure; and optionally, one or more reaction tubes with solid or liquid reagents;

In another preferred embodiment, the method and kit of parts can be used for extracting nucleic acids from allergens selected from cereals and products thereof, chickpea and products thereof, casein, almond and products thereof, cashew and products thereof, peanut and products thereof, hazelnut and products thereof, macadamia and products thereof, mustard and products thereof, soya and products thereof, sesame and products thereof, walnut and products thereof, pistachio and products thereof, lupine and products thereof, celery and products thereof, fish and products thereof, crustaceans and products thereof. In another embodiment, the method and kit of parts may be used for extracting nucleic acids from genetically modified organisms.

Another preferred embodiment relates to the use of the composition according to the present disclosure in the analysis of nucleic acids by polymerase chain reaction.

By addition of a single tablet comprising the mixture of solids according to the present disclosure, and 70 to 95° C. hot water there is no longer a need for additional enzymes, organic solvents, surfactants, etc. for obtaining a disruption of the sample matrix. The composition tablet or capsule can be used with all tested food matrices because the high osmotic strength due to the large amount of salt in combination with high temperatures leads to a release of nucleic acids from all biological matrices. The slightly acidic phosphate buffer on the other hand stabilizes the nucleic acids chains even in aqueous solutions of up to 95 degrees Celsius. Most importantly, one method can be used with all types of biological matrices as different a leather, furs, textiles, chocolate, cereals, nut containing materials, meat, etc. This is particularly important for the many processed food and chocolate bars.

An important advantage is the establishment of a routine procedure in the analysis of samples with different physico-chemical properties such as foods rich in lipids (chocolate/nut pastes), proteins (meats), polysaccharides (cereals) and, notably, mixtures thereof. It is no longer necessary to adapt the method to the food matrix which again requires laboratory experience and additional equipment. By way of the present disclosure, anyone without extensive laboratory experience is thus able to perform an extraction of nucleic acids from any biological sample, even when the samples are of different origin. Total standardisation of nucleic acid extraction from virtually any biological or food matrix is achieved with the disclosed composition (tablet) and method.

The conventional CTAB or organic solvent extraction is further associated with health risks due to the organic solvents and surfactants. Moreover, the conventional methods require a complete removal of added solvents, reagents and surfactants to avoid interference with the polymerase chain reaction. These include ionic detergents such as sodium deoxycholate, sarkosyl and SDS, ethanol and iso-propanol, phenol and others. Biological samples types known to contain inhibitors include blood, fabrics, tissues and soil. Typical PCR inhibitors endogenous to biological samples are bile salts (feces), complex and other polysaccharides (feces, plant materials), collagen, myoglobin, hemoglobin, immunoglobins and heme (meat and blood), humic acid (soil, plant materials), melanin and eumelanin (hair, skin), calcium ions and proteinases (milk, bone). The present disclosure overcomes the problems commonly associated with those endogenous and added PCR inhibitors, first by not requiring any organic solvent or surfactant and, second, by removal of those inhibitors together with the hydrated magnesium silicate particles. Without wishing to be bound by theory, it is assumed that the disclosed heat-step leads to a complete denaturation of proteinaceous polymerase inhibitors whereas hydrophobic, lipophilic and acidic inhibitors become adsorbed on the magnesium silicate particles. The silicate powder acts as genomic DNA stabilizer and binds at least a portion of lipids, proteins, polysaccharides and salts contained in the matrix, precipitating and removing them from the fraction containing the genomic DNA.

Assessment of the nucleic acid content and/or presence of inhibitors in a sample is carried out based on the Ct value obtained by quantitative real-time polymerase chain reaction. Lower Ct values indicate that the DNA polymerase requires fewer cycles to amplify target DNA in the sample. The method and kit of the disclosure allows for rapid, safe and economically advantageous nucleic acid extraction from food matrices, without the disadvantages of conventional approaches.

As mentioned, the buffering agent is responsible for creating an osmotic shock, forcing the cytoplasm and, in particular, the cell nucleus to release its content into the extraction medium preserving nucleic acid integrity for subsequent analysis. A desalting step is therefore recommended prior PCR analysis to reduce the salt concentration in the reaction. This can be carried out by size exclusion chromatography, ultra filtration or conventional DNA binding chromatography. Alternatively, the PCR sample may also be simply diluted to lower the salt concentration to acceptable levels.

Further advantages, goals and embodiments of the invention become apparent from the attached drawings, representative examples and claims. The invention however shall not be limited by the examples but has been defined in the claims.

DETAILED DESCRIPTION OF THE INVENTION

Figure 1:
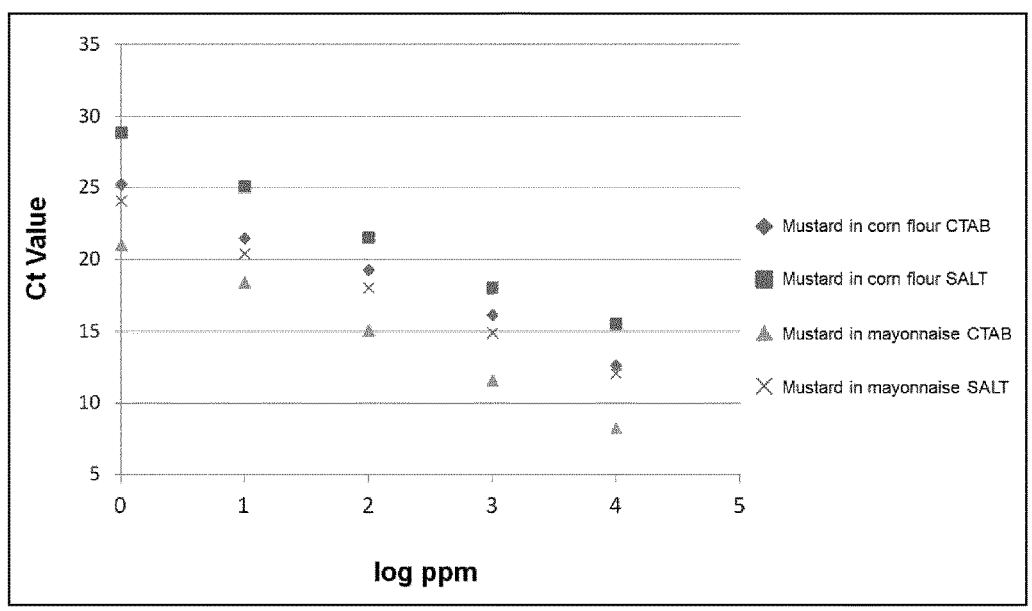
FIG. 1 is a diagram showing a comparison of the cycle threshold for mustard detection by PCR in samples with known mustard amounts (log ppm).

The composition for use in extracting and purifying nucleic acids from food samples is a mixture of solids comprising from 10 to 40 percent by weight particles of water-insoluble hydrated magnesium silicate having a median particle size from 0.8 to 2.5 µm, and from 20 to 70 percent by weight of crystalline salt which is readily water-soluble to produce a saline phosphate buffer having a pH from 5.5 to 7.0 at 70 to 95 degrees Celsius. A mixture of solids is a combination of solid substances in form of powder, granules, particles or crystals without a liquid solvent. The water-insoluble hydrated magnesium silicate is preferably a hydrated magnesium silicate or fine talc in the form of a fine talk powder or finely granulated. Said hydrated magnesium silicate powder may have a median particle size in the range of 1.0 to 2.0 µm, preferably from 1.2 to 1.5 µm; a median diameter $D_{50}$ in the range of 0.8 to 2.5 µm; and a density of 2.6 to 2.8 $g/cm^3$. The insoluble silicate powder has therefore a large surface for adsorption of lipids, complex sugars and other potential polymerase inhibitors.

The phosphate buffer salt may be present in the mixture of solids as fine crystals or in granulated form and its composition preferably is as follows: NaCl 137 mmol/L, $Na_2HPO_4.2 H_2O$ 10 mmol/L, KCl 2.7 mmol/L, $KH_2PO_4$ 2 mmol/L. The phosphate buffer salt shall give after dissolving a hypertonic solution so that the nucleic acids are also released from the biological sample through the resulting osmotic shock. The composition of the phosphate buffered saline is preferably such that it gives a pH from 5.5 to 7 at a water temperature from 70 to 95 degrees Celsius.

The particles of the mixture of solids may be pressed or compressed and portioned to obtain a tablet. A tablet is made up of the mixture of solids only. A capsule can be made of gelatine and filled with the mixture of solids, without being pressed. The compacting of the composition can be performed by any conventional device for powder compression known by the skilled person in the art.

The swellable hydrophilic colloid may be present in the mixture in granulated or microcrystalline form. Suitable swellable material for rapid dissolving the tablet or capsule powder may be chosen from cellulose, carboxy-methyl cellulose, cellulose derivatives, alginate, starch, xanthan gum, arabic gum, guar gum or mixtures thereof. The swellable hydrophilic colloid can both facilitate the compacting of the composition as well as the dispersion of the mixture of solids upon contact with water. The swellable material must be free of contaminants, in particular animal nucleic acids, genetically modified organisms and allergens. Moreover, the tablet may contain one or more non-chaotropic detergents and heat-stable enzymes. The tablet may be optionally coated with a film, preferably made of cellulose, preferably cellulose derivatives, most preferred hydroxypropyl methylcellulose (HPMC) in order to keep out moisture and for avoiding tablet debris.

The tablet or capsule may comprise a mixture of solids made up from 10 to 25 percent by weight of water-insoluble hydrated magnesium silicate particles; from 45 to 70 percent by weight phosphate buffered salt; and from 20 to 30 percent by weight of a swellable hydrophilic colloid effective to assist the dispersion of the mixture of solids in water.

The standard method of isolating DNA from a diversity of samples for subsequent PCR analysis may comprise the following steps: a predefined weight or volume amount from 10 to 100 g (mL) of the sample is prepared using a scale or pipette. The sample can preferably be dissociated using a grinder or blender resulting in a small particles, solution or dispersion. A portion from 50 mg to 5 g of the dissociated sample can be weighted using a scale and, with a spatula, transferred into a vessel having a safe lock to avoid contamination and spillage. A predefined amount of the mixture of solids from 50 mg to 1 g can be added to the sample to obtain a weight ratio of solids in the vessel from 1:5 to 5:1 of mixture of solids to sample. An amount of water, previously heated at a temperature of 70 to 95 degrees Celsius using a boiler may then be added to dissolve the buffer components of the mixture of solids to obtain an aqueous phosphate buffered saline solution having a pH from 5.5 to 7.0 and a salt concentration of 0.6 to 1.2 Mol/L. The dispersion of the sample and the mixture of solids in phosphate buffered saline can be obtained by vortexing or shaking the sample from 1 second to 120 seconds. Alternatively, a mixer may be used, preferably a piston mixer. The solution or dispersion may be heated at temperature from 70 to 95 degrees Celsius using anyone of water bath, thermoblock, oven or any other heating unit such as microwave. The temperature treatment may take from 1 minute to 30 minutes, preferably for about 5 minutes to 20 minutes, to release the nucleic acids from the cellular materials and other water-insoluble components of the sample. Due to the excess of salt and phosphate even a prolonged treatment of the nucleic acids at 95 degrees Celsius proved having no noticeable adverse effect on the stability of the DNA, if subsequently tested by PCR. A release of nucleic acids is considered having taken place when cellular structures (membranes, organelles, etc.) are so disrupted so that an interaction of nucleic acids with structural proteins, lipids and polysaccharides no longer occurs. The osmotic difference created by the hypertonic solution also furthers a release of the nucleic acids from the cell nuclei. The high temperatures not only disrupt cell walls and lead to a denaturation of proteins, they also cause an increase solubilisation of lipids and polysaccharides which are however adsorbed and precipitated in a binding status on the water-insoluble magnesium silicate particles. At least, they get bound primarily by the water-insoluble hydrated magnesium silicate particles and less by inner walls of the vessel. A separation of the mixture of solids from the aqueous phase together with the water-insoluble components can preferably be performed by centrifugation (e.g. table top centrifuge) or filtration (e.g. cellulose filters). The aqueous supernatant or filtrate containing soluble nucleic acids free of DNA polymerase inhibitors can be pipetted or decanted into a clean vessel.

The standard method of nucleic acids isolation is then usually followed by a desalting step, which can be carried out using size exclusion chromatography, ultra-filtration, or affinity chromatography such as a commercial silica-based nucleic acid extraction column. Alternatively, the nucleic acid sample may be diluted so that the salt concentration is reduced to acceptable levels and the sample is suitable for PCR analysis.

Another aspect relates a kit of parts for extraction and detection of nucleic acids from a food sample and may comprise a tablet comprising a known amount of a ready-to-use composition (mixture of solids) for extracting nucleic acids in accordance with the present disclosure and optionally, one or more reaction tubes with solid or liquid reagents.

In a preferred embodiment of the disclosure, the composition, method and kit of parts for nucleic acid extraction may be used for isolating and characterizing nucleic acids from raw and/or processed animal and plants materials and processed products thereof. Raw animal and plant material means portions or fragments of the organisms from which they derive, without undergoing previous mechanical dissociation, chemical or thermal treatment. Processed animal, plant material and products thereof imply matter that has been mechanically dissociated and/or chemically or thermally treated, so that its original form and physical properties have been altered.

In another preferred embodiment, the composition, method, and kit of parts for nucleic acid extraction can be used for isolating nucleic acids characteristic for potential allergens present in cereals and products thereof, chickpea and products thereof, casein, almond and products thereof, cashew and products thereof, peanut and products thereof, hazelnut and products thereof, macadamia and products thereof, mustard and products thereof, soya and products thereof, sesame and products thereof, walnut and products thereof, pistachio and products thereof, lupine and products thereof, celery and products thereof, fish and products thereof, crustaceans and products thereof. Animals, plants or microorganisms are sources for biological allergens. The composition, method, and kit of parts can further be used for isolating nucleic acids characteristic for genetically modified organisms, pathogens, *Salmonella* spp., *Listeria* spp. *Shigella* spp., *Campylobacter* spp., *Cronobacter*, *Clostridium* spp., *Legionella* spp., *Enterobacteriaceae*, *Escherichia* spp. A genetically modified organism (GMO) is an organism, such as bacteria, yeast, insects, plants, fish, and mammals, whose genetic material has been changed using genetic engineering techniques. A pathogen means any organism, such as bacteria, fungi or protozoans that can induce a disease in its host organism.

In another preferred embodiment, the composition, method, and kit of parts for nucleic acid extraction may be used for the isolation of nucleic acids from fecal samples, preferably human and animal fecal samples.

The detection and quantification of foreign material in food samples by a polymerase chain reaction is known by person skilled in the art. The purification of nucleic acids from complex matrices however required an addition of various disrupting enzymes, organic solvents, and surfactants. Sufficiently pure DNA means here "free of DNA polymerase specific inhibitors" so that an amplification of the extracted DNA is obtained. The DNA extraction and purification efficiency may be described by the so-called cycle threshold (Ct), which is the number of polymerase reactions needed to amplify a template DNA in the sample to detection level. Lower Ct values mean fewer number of cycles required to amplify the template DNA and, therefore, higher detection sensitivity.

Beyond the analysis of food samples, detection of fur from domestic animals (i.e. cat, dog) in falsely labelled garment products is also possible. Also other solid materials (e.g. textiles, wiper tissues, etc.) can effectively be subjected to nucleic acid extraction as described. The composition, method and kit of the disclosure can be uniformly applied to all types of food samples, considerably reducing the steps of nucleic acid extraction as well as minimizing pipetting errors and contamination. Most importantly, it can thus be applied to unknown sample matrices and it is no longer necessary to use different nucleic acid purification methods for the diversity of samples. In other words, the method must no longer be tested in advance on a sample. The method of the present disclosure is sensitive and reproducible for different laboratories and samples as well as different PCR reactions, allowing the establishment of standard curves for nucleic acid determination from animals, plants, bacteria, genetically modified organisms and allergens in a sample.

Further embodiments, objects and advantages of the invention will become apparent from a study of the examples given below.

EXAMPLES

Example 1

Composition for DNA Extraction and Salt/Talcum Tablet

Pharmaceutical grade talcum powder form was used in the preparation of the DNA extraction tablets. The talcum had a median particle size of 1.2 μm, a median diameter $D_{50}$ of 0.65 μm and a density of 2.8 g/cm$^3$. The talcum powder (hydrated magnesium silicate) had the following composition: $SiO_2$ (61.5%), MgO (31.0%), CaO (0.4%), $Fe_2O_3$ (0.6%), ($Al_2O_3$) 0.5%, with a pH of 8.8. The second component was phosphate buffered saline according to Dulbecco (1× PBS=NaCl 137 mmol/L, $Na_2HPO_4$.2 $H_2O$ 10 mmol/L, KCl 2.7 mmol/L, $KH_2PO_4$ 2 mmol/L) and added as a microcrystalline salt. Pharmaceutical grade swellable microcrystalline cellulose free of contaminants was used as disintegration agent. All three components were compressed into a tablet using a stamping press. The "salt" tablet had a total unit weight of 117 mg and consisted of talcum particles: 20 mg (17.1%); crystalline PBS salt: 68 mg (58.1%); swellable cellulose: 29 mg (24.8%). The tablet was sized for the extraction of food samples having about 200 mg.

Example 2

DNA Extraction from Complex Food Samples ("Salt Protocol")

DNA extraction: 10 g of sample (Bockwurst sausage in casing, Farmer's breakfast (type of ham), red sausage, pizza salami, Bolognese sauce, smoked sausage, chicken cordon bleu, chicken noodle soup and animal feed) was obtained and mechanically homogenised using a grinder (mixer) with rotating knifes. When the grinded sample turned liquid it was further homogenized using a glass homogenizer with a piston. 200 mg homogenous sample was transferred into a 2 mL Eppendorf tube using a pipette or a spatula. A (1) sample extraction tablet of Example 1 was added together with 1 mL aqua dest. The PBS concentration in the resulting sample solution was about 5 times. The tube was vortexed for 5 seconds and placed in a water bath at 95 degrees Celsius for 20 minutes. Following centrifugation at 14.000 rpm, RT for 5 minutes, the pellet with the precipitate was discarded and the clear supernatant used for further analyses.

Desalting: The supernatant was desalted using a DNA affinity column (Centrispin, Genaxxon) in accordance with the manufacturer's instructions. In brief, 100 µL supernatant was added to 500 µL binding buffer and the volume (600 µL) loaded onto an equilibrated DNA spin column, followed by 14.000 rpm for 2 minutes at RT. The flow-through was discarded, the column washed with 700 µL washing buffer and the sample DNA eluted with 50 µL elution buffer.

Example 3

Conventional CTAB DNA Extraction

For comparative purposes, the same homogenized samples were also subjected to DNA extraction using the CTAB DNA extraction protocol. To this end, 100 ml CTAB lysis buffer was prepared by mixing 2.0 g CTAB (hexadecyl trimethylammonium bromide), 10.0 ml 1 M Tris pH 8.0, 4.0 ml 0.5 M EDTA pH 8.0, 28.0 ml 5 M NaCl, 40.0 ml $H_2O$. The pH was adjusted with HCl to pH 8.0 and aqua dest. added up to a volume of 100 ml. 2 g homogenised sample was mixed with 10 ml CTAB lysis buffer and 25 µl proteinase K (20 mg/ml) and incubated overnight at 60 degrees Celsius under mild shaking. Following centrifugation at 4000 g, RT for 5 minutes, the first pellet was discarded and the supernatant again centrifuged at 14000 g, RT for 10 minutes. The supernatant was then extracted with an equal volume of chloroform. 600 µl aqueous phase was mixed with 1.2 ml CTAB precipitation buffer (5 g/L CTAB, 0.04 mol/L NaCl), the DNA precipitated at RT for 60 minutes, followed by centrifugation at 14000 g, ambient temperature for 10 minutes. The supernatant was discarded and the DNA pellet taken up in 350 µl 1.2 mol/l NaCl solution. After another extraction with 350 µl chloroform, the DNA in the aqueous phase was again isopropanol precipitated at room temperature for 20 minutes. After centrifugation, the supernatant was discarded and the DNA pellet spin-washed with 500 µl cold 70% ethanol and dried at ambient temperature. The dried DNA pellet was dissolved in 100 µl 0.1× TE. RT-PCR and Ct value determination was performed as described in Example 2.

Example 4

Real-Time PCR, Ct Value, and Assessment of PCR Inhibition

RT-PCR was performed using the RotorGene instrument (Qiagen) in accordance with manufacturer's instructions. The PCR was performed in a 20 µl volume comprising 10 µl 2× SensiFAST™ Multiplex Master Mix (Bioline GmbH, Luckenwalde. Del.), 200 nM reference DNA, 400 nM primers, and 10 µl DNA extract. The SensiFast Multiplex MasterMix consists of a buffer system, $Mg^{2+}$, all four dNTPs and DNA polymerase. The PCR thermocycler was programmed having one initial incubation step at 95° C. for 5 min followed by 45 cycles of incubation at 95° C. for 15 sec, 60° C. for 15 sec and 72° C. for 10 sec. PCR were performed in duplicates. The Ct value was determined by the Rotor-Gene software using a threshold of 0.02.

For assessment of PCR inhibition (inhibition control) 2 ng DNA extracted and prepared in accordance with example 2 ("Salt") or conventional example 3 (CTAB) from pork beef, chicken, turkey, ruminant, etc. was added in a volume of 10 µl without primers. Otherwise, specific primers for detection of target DNA from pork, beef, chicken, turkey, ruminant were added.

The relative PCR inhibition by the sample can then be taken from the Ct values for the reference DNA amplification (inhibition control). The results are shown in Table 1.

TABLE 1

| Matrix | Species | Test system Ct Salt | Test system Ct CTAB | Inhibition control Ct Salt | Inhibition control Ct CTAB |
|---|---|---|---|---|---|
| Bockwurst sausage in casing | Pork | 18.13 | 22.20 | 30.35 | 29.55 |
| Farmer's breakfast | Pork | 18.93 | 23.04 | 29.49 | 29.39 |
| Red sausage | Pork | 20.86 | 24.99 | 31.76 | 29.75 |
| Pizza Salami | Pork | 19.83 | 22.01 | 28.32 | 28.23 |
| Bolognese sauce | Beef | 31.32 | 34.97 | 30.61 | 30.80 |
| Smoked sausage | Beef | 22.65 | 25.84 | 30.41 | 30.95 |
| Chicken cordon bleu | Chicken | 20.71 | 21.73 | 28.52 | 29.70 |
| Chicken soup (chicken noodle soup) | Chicken | 20.00 | 22.12 | 28.81 | 28.57 |
| Chicken cordon bleu | Turkey | 20.09 | 21.84 | 28.83 | 28.85 |
| Animal meal | Ruminant | 32.79 | 32.26 | 31.36 | 31.49 |

The inhibition control experiments show very similar Ct values regardless of the sample matrix from which the DNA was prepared and regardless of the method of purification (example 2 "Salt" or example 3 "CTAB").

The results suggests that the herein disclosed DNA purification methods (talc/PBS salt and CTAB protocol) are equivalent and can be used for many different food matrices as they end up in DNA probes equivalent in terms of their amplification properties ("no DNA polymerase inhibition"). This confirms the high performance and feasibility of the talc/PBS salt extraction protocol while it is quicker (extraction and RT-PCR can be done on the same day), less laborious and does not require the use of expensive and nasty chemicals. No chaotropic chemicals such as CTAB or urea are required and no extractions with organic solvents such as chloroform must be done which require the use of a laboratory fume hood for health reasons.

Most importantly, the quality of the target DNA (tested for pork, chicken, turkey, beef or ruminant) was regularly better, independently of the original food matrix, when using the talcum/PBS protocol. While the sample solutions were equivalent with respect to the amount of PCR inhibitors, the lower Ct values for the target DNA suggest that the isolated target DNA in accordance with example 2 may have had a better quality than DNA extracted and purified in accordance with the CTAB protocol.

Example 5

Effects of Talc

Soya flour, soya lecithin and a commercial seasoning were homogenised as described and sample DNA extracted and isolated in accordance with the method of Example 2. For comparison just cellulose and PBS salt (without talc) was added prior extraction. After centrifugation, two well defined phases were observed in the DNA preparations with added talcum/PBS, say a clear supernatant and a defined precipitation pellet, whereas the supernatant in the preparation without talc was still turbid. The supernatant was in each case used for DNA purification as described. Real-time PCR, and Ct values for soja and celery DNA were determined as described above. For results, see Table 2.

TABLE 2

| Matrix | PCR-Parameter | Without talc | With talc |
|---|---|---|---|
| Soya flour | Soja | 21.7 | 21.1 |
| Soya lecithin | Soja | 33.5 | 30.7 |
| Seasoning | Celery | 25.5 | 25.1 |

In each case, the added talc had adsorbed and precipitated DNA polymerase inhibitors present in the lecithin matrix or the seasoning as shown by the lower Ct values. The addition of talc further facilitates the handling of samples containing plenty of phospholipids, fatty acids and triglycerides.

Example 6

DNA Extraction from Soya Lecithin

Soya lecithin was homogenised and DNA extracted and purified as described in example 2 (talc/PBS salt) or comparative example 3 (CTAB). The DNA yields were analysed by measuring the OD at 280 nm and the OD ratio at 260 nm/280 nm. The results are shown in Table 3.

TABLE 3

| | Salt/Talc | CTAB |
|---|---|---|
| OD Value 260 nm | 0.017 | 0.118 |
| Ratio 260 nm/280 nm | −3.2 | 1.67 |
| DNA concentration | 0.9 ng/μL | 5.9 ng/μL |

The CTAB protocol gave a higher DNA yield and purity (protein/DNA). However, these advantages did not hold when the DNA was subjected to PCR analysis.

Real-time PCR was performed as described in example 4. The target DNA was for contamination with genetically modified Roundup Ready™ soya, say pairs of primers were added for detection of 35S (35S-promoter, originated from cauliflower mosaic virus), nos (nopaline synthase-terminator, derived from *Agrobacterium tumefaciens*), RRS (5-enolpyruvylshikimate-3-phosphate synthase, obtained from *A. tumefaciens* strain CP4). The PCR inhibition control conditions were done as described in Example 4. See Table 4 for results.

TABLE 4

| Test gene | Test system Ct Value SALT | Test system Ct Value CTAB | Inhibition control Ct Value SALT | Inhibition control Ct Value CTAB |
|---|---|---|---|---|
| Soya | 28.67 | 31.64 | 29.5 | 31.2 |
| 35S | 36.78 | 37.85 | 29.42 | 32.19 |
| NOS | 39.53 | 39.09 | 29.83 | 31.6 |
| RRS | 39.54 | 34.93 | 30.32 | 30.36 |

The inhibition control experiments again resulted in similar Ct values. While no major differences were found, the slightly larger inhibition in samples prepared in accordance with the CTAB protocol suggests that traces of added CTAB, which also has DNA polymerase inhibiting activity, might have been present in those samples whereas talcum and PBS salt can be more easily and reliably removed.

The talcum/PBS protocol resulted in generally lower Ct values than the CTAB protocol. Despite the lower DNA yields by the talc/PBS protocol (cf. table 2) the Ct values for the analyzed transgenes were equivalent for both DNA extraction methods. The Ct values were different for the various genes investigated which indicates different amounts of contamination.

Example 7

Detection of Genetically Modified Organisms in Cereals and Plants

Corn grains, soya protein isolate, soya beans, multi-cereal toast bread, mustard flour, rape seeds and animal feed were analyzed as described above. Added primers were for detection of 35S, RRS, FMV (promotor from figwort mosaic virus), nos, Ctp2 (CTP2-CP4EPSPS, intersection of chloroplast-transit peptide to 5-enolpyruvyl-shikimate-3-phosphate synthase; from *Arabidopsis thaliana* and *Agrobacterium* sp. resistence to herbicide Roundup Ready) and CAMV (CaMV, 35S promoter from the cauliflower mosaic virus). See Table 5 for results.

TABLE 5

| Matrix | Gene | Test system Ct Salt | Test system Ct CTAB | Inhibition control Ct Salt | Inhibition control Ct CTAB |
|---|---|---|---|---|---|
| Corn | 35S | 29.27 | 30.59 | 29.61 | 29.48 |
| Soya protein isolate | RRS | 31.36 | 34.69 | 31.46 | 31.34 |
| Soya | FMV | 36.98 | 38.21 | 31.44 | 33.24 |
| Multi-cereal toast | nos | 27.40 | 26.91 | 30.70 | 29.58 |
| Mustard flour | Ctp2 | 33.40 | 34.10 | 30.27 | 31.42 |
| Rape seed | 35S | 33.28 | 37.44 | 30.02 | 29.10 |
| Animal feed | CAMV | 30.19 | 30.48 | 29.99 | 30.53 |

The inhibition controls gave again similar Ct values for the DNA reference so that both DNA extraction methods could be used with all tested sample matrices. However, the Ct values obtained for target DNAs suggest that the DNA purified using the talc/PBS salt is generally more intact ("better-quality DNA yield") than DNA prepared from a sample matrix using the CTAB extraction protocol.

Example 8

DNA Extraction from Complex Vegetables/Plant Samples

Raw almond paste, biscuit (without flavouring), rice crispies, poppy seed mix and dark hazelnut paste examined.

Sample DNA was extracted and purified as described. Results are shown in Table 6.

TABLE 6

| Matrix | Species | Test system Ct Salt | Test system Ct CTAB | Inhibition control Ct Salt | Inhibition control Ct CTAB |
|---|---|---|---|---|---|
| Raw almond paste | Almond | 21.94 | 22.20 | 28.94 | 30.80 |
| Biscuit (no flavouring) | Almond | 25.94 | 27.03 | 32.17 | 32.79 |
| Rice crispies | Corn | 20.62 | 21.34 | 27.71 | 28.23 |
| Poppy seed mix | Corn | 29.16 | 27.79 | 30.78 | 31.74 |
| Dark hazelnut paste | Soya | 38.36 | No Ct | 31.55 | 33.23 |

The Ct values for the reference DNA were again similar for all sample preparations and food matrices, while we again noted less inhibition in the samples prepared in accordance with talc/PBS salt protocol. The results further suggest better quality DNA yields for the talc/PBS salt protocol than with the CTAB protocol since traces of soya were detectable the tested "dark hazelnut paste" which were not found in the comparative DNA preparation using the CTAB protocol.

Example 9

DNA-Based Detection of Allergens in Food Samples

Milk-based spread comprising chocolate/hazelnut flakes, a spraying agent for smoked pork, hazelnut pulp (thermally treated at 166° C.), swab, almond (grinded, size pieces 1-2 mm), parsley (grinded), condiment mixture and salmon au gratin were tested for DNA from typical sources of allergens (hazelnut, mustard, pecan, fish, peanut, and celery). DNA extraction, RT-PCR and Ct values were analogous as in Examples 2, 3 and 4. Results are shown in Table 7.

TABLE 7

| Matrix | Allergen | Test system Ct Salt | Test system Ct CTAB | Inhibition control Ct Salt | Inhibition control Ct CTAB |
|---|---|---|---|---|---|
| Milk spread with chocolate-hazelnut flakes | Hazelnut | 29.95 | 28.07 | 31.72 | 32.48 |
| Spraying agent for smoked pork | Mustard | 38.19 | 38.78 | 32.44 | 31.85 |
| Hazelnut pulp (thermally treated at 166° C.) | Pecan | 37.73 | 40.71 | 32.35 | 32.69 |
| Swab | Fish | 31.91 | 32.89 | 26.74 | 32.11 |
| Almond (grinded 1-2 mm size) | Peanut | 31.47 | 34.04 | 34.59 | 37.31 |
| Parsley (grinded) | Celery | 27.02 | 24.65 | 32.09 | 31.78 |
| Condiment mixture | Mustard | 24.49 | No Ct | 32.80 | No Ct |
| Salmon au gratin | Fish | 26.74 | 32.11 | 31.91 | 32.89 |

The Ct values for the internal DNA reference (inhibition control) were similar across all food matrices, except for the condiment mixture. The results again suggest better quality DNA yields for the talc/PBS protocol since no mustard DNA nor reference DNA was detectable in the condiment mixture when extracted using the CTAB protocol.

Example 10

Sensitivity and Linearity

Samples of corn flour with known amounts of mustard (1, 10, $10^2$, $10^3$ and $10^4$ ppm) were processed as described in Example 2 and the Ct values for DNA from a) normal and b) yellow mustard determined (see FIG. 1) as described. The same was also done for samples of mayonnaise with known amounts of mustard (1, 10, $10^2$, $10^3$ and $10^4$ ppm). All Ct measurements were done in duplicates and the average value used for calculating linearity and sensitivity of the detection. The results are shown in Table 8.

TABLE 8

| Parameter | Mustard | | Yellow mustard | | |
|---|---|---|---|---|---|
| Matrix | Ct-Value CTAB | Ct-Value SALT | Ct-Value CTAB | Ct-Value SALT | log ppm |
| Mustard in corn flour 10000 ppm | 12.62 | 15.55 | 23.97 | 25.96 | 4 |
| Mustard in corn flour 1000 ppm | 16.14 | 18.04 | 27.22 | 28.74 | 3 |
| Mustard in corn flour 100 ppm | 19.26 | 21.53 | 30.06 | 33.1 | 2 |
| Mustard in corn flour 10 ppm | 21.46 | 25.09 | 32.76 | 35.11 | 1 |
| Mustard in corn flour 1 ppm | 25.22 | 28.88 | | | 0 |
| Mustard in mayonnaise 10000 ppm | 8.33 | 12.08 | 20.1 | 23.23 | 4 |
| Mustard in mayonnaise 1000 ppm | 11.6 | 14.92 | 23.23 | 26.05 | 3 |
| Mustard in mayonnaise 100 ppm | 15.08 | 18.04 | 26.42 | 29.41 | 2 |
| Mustard in mayonnaise 10 ppm | 18.44 | 20.42 | 29.97 | 32.23 | 1 |
| Mustard in mayonnaise 1 ppm | 21.03 | 24.10 | 32.51 | 36.38 | 0 |

Figure 2:
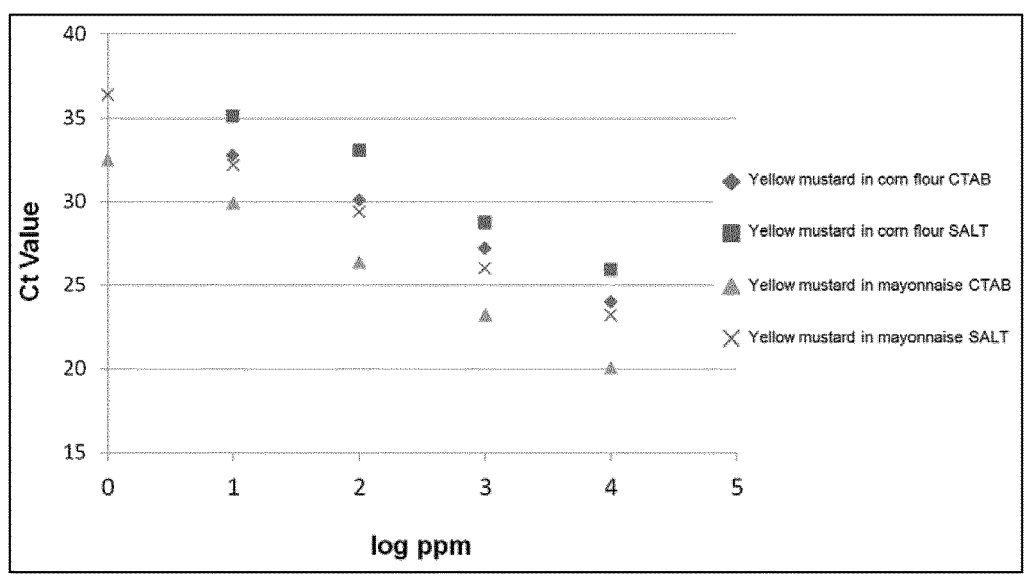
FIG. 2 is a diagram showing a comparison of the cycle threshold for yellow mustard detection by PCR in samples with known yellow mustard amounts (log ppm).

The Ct values for the presence of either mustard or yellow mustard in corn flour and mayonnaise have been plotted in FIGS. 1 and 2. The results show a linear behaviour of DNA detection by real-time PCR, when the DNA was extracted and purified according to the talc/salt protocol. The linearity was comparable to CTAB extracted samples. Importantly, this was found for two very different food matrices, namely for corn flour which is rich in polysaccharides and mayonnaise which has a high content of lipids, fatty acids and oil. The extraction with talc/salt tablets further allowed a detection of extremely low amounts of contaminant, down to 1 ppm. While the detection sensitivity was somewhat lower, it was comparable to that of CTAB. The linear behaviour therefore allows for the establishment of standard curves which renders possible an estimation of the absolute amount of contaminant within a food matrix with great confidence.

Example 11

Quantitative Determination of Foreign Material in Food Samples

DNA from meatball, rape seed, pastry, sausage, durum wheat semolina and durum wheat flour were obtained as described in Examples 2 and 3. Foreign materials were identified using specific primers for buffalo, GT73 (marker of genetically modified rape seed, RRS, pork and wheat. A housekeeping gene was selected accordingly and specific primers used in each condition. The relative percentage of foreign DNA in the total DNA sample were thus determined for different food matrices using a conventional DNA preparation and the one disclosed herein. Results are shown in Table 9

TABLE 9

| Matrix | PCR-Parameter | SALT | CTAB |
|---|---|---|---|
| Meatball | Buffalo | 0.02% | 0.02% |
| Rape seed | GT73 | 0.03% | 0.03% |
| Rape seed | GT73 | 0.77% | 0.61% |
| Pastry | RRS | 0.18% | 0.19% |
| Sausage | Pork | 1.88% | 1.97% |
| Sausage | Pork | 0.15% | 0.33% |
| Durum wheat semolina | Wheat | 19% | 12% |
| Durum wheat flour | Wheat | 5.10% | 5.20% |

The results in Table 9 confirm a sensitive, quantitative detection of foreign material when the sample matrices were in processed and worked-up in accordance with the talc/salt protocol. The obtained values are very similar for either extraction and purification protocol. Consistent detection sensitivity is observed for the given sample matrices.

Example 12

Quantitative Determination of GMO DNA in Animal Feeds

Samples from 12 different commercially available animal feeds were DNA-analysed as described above. Primers for genetically modified soybean and the RRS gene were used. Primers for a housekeeping gene were chosen for quantitating total DNA. Results are shown in Table 10 below.

TABLE 10

| Matrix | PCR-Parameter | SALT | CTAB |
|---|---|---|---|
| Animal feed 1 | MON89788 | 0.16% | 0.10% |
| Animal feed 1 | RRS | 0.14 | 0.1 |
| Animal feed 2 | RRS | 42% | 54% |
| Animal feed 3 | RRS | 0.10% | 0.13% |
| Animal feed 4 | RRS | 0.11% | 0.09% |
| Animal feed 5 | RRS | 0.35% | 0.46% |
| Animal feed 6 | RRS | 0.04% | 0.07% |
| Animal feed 7 | RRS | 0.73% | 0.85% |
| Animal feed 8 | RRS | 49% | 47% |
| Animal feed 9 | RRS | 49% | 57% |
| Animal feed 10 | RRS | 62% | 58% |
| Animal feed 11 | RRS | 43% | 47% |

The results confirm that the talc/salt-based DNA extraction method provides sample which can reliably be used for determining the relative content of biological materials in highly processed feed matrices.

Example 13

Bacterial DNA Extraction and Detection from Food Enrichment Cultures

Pre-enrichment cultures were prepared by inoculating 225 mL buffered peptone water (BPW) broth (1:9 ratio), warmed at 37° C., with a probe. The probes tested were a wiper/cloth (Kleenex™ tissue), water from cooling circuit, chocolate, dark chocolate coating, drinking water, beef (round robin 01-03), sesame, onion mettwurst sausage, dairy products, duck meat in stripes, turkey breast, marinated duck meat, whole milk and turkey thigh meat. The enrichment culture was incubated at 37° C. for 18 hours under shaking. 900 µL enrichment culture was mixed with 100 µL of a dilution from an overnight culture of *Salmonella* spp., *Listeria monocytogenes, Cronobacter* spp, and *Campylobacter* spp., so that it contained 103 colony forming units (cfu) per experimental condition. 200 µL post-spiked culture (200 cfu) was subjected to DNA extraction in accordance with Examples 2 or 3. When extracted in accordance with the talc/salt protocol, the procedure was followed as described up to the first centrifugation step. A dilution (1:20) of the supernatant was however directly subjected to PCR analysis. RT-PCR and Ct values were determined as in Example 4. Specific primers for detection of *Salmonella* spp., *Listeria monocytogenes, Cronobacter* spp., and *Campylobacter* spp. were used.

In case of the comparative CTAB extraction, the solution for bacterial DNA extraction contained 2% CTAB, 100 mM Tris-HCl, pH 8, 20 mM EDTA, 1.4 M NaCl, 0.2% β-mercaptoethanol, 0.1 mg proteinase K. 0.8 mL CTAB buffer at 60° C. was added to 200 µL enriched culture sample and incubated at 60° C. for 1 hour with regular movement every 10 minutes. 0.8 mL chloroform/isoamylalcohol (24:1) was added, mixed for 2 minutes, followed by centrifugation at 14.000 rpm for 10 minutes at 4° C., to obtain two phases. The upper clear aqueous phase above a white interface layer was withdrawn and used for DNA purification and desalting as described in Example 2. Qualitative RT-PCR and Ct value determination were performed as described in Example 4. The results are shown in Table 11. The Ct values of the test systems indicate whether or not DNA of the respective pathogen was present in the sample taken.

TABLE 11

| Matrix | Pathogen | Test system Ct Salt | Test system Ct CTAB | Inhibition control Ct Salt | Inhibition control Ct CTAB |
|---|---|---|---|---|---|
| Wiper | *Salmonella* spp. | 33.23 | 36.55 | 28.89 | 31.06 |
| Wiper | *Salmonella* spp. | 31.96 | 31.66 | 29.59 | 29.17 |
| Water from cooling circuit | *Salmonella* spp. | 25.90 | 27.02 | 29.84 | 30.44 |
| Chocolate | *Salmonella* spp. | 20.48 | 18.97 | 27.83 | 28.25 |

TABLE 11-continued

| Matrix | Pathogen | Test system Ct Salt | Test system Ct CTAB | Inhibition control Ct Salt | Inhibition control Ct CTAB |
|---|---|---|---|---|---|
| Dark chocolate coating | Salmonella spp. | 23.66 | 21.68 | 29.25 | 27.99 |
| Drinking water | Salmonella spp. | 26.91 | 27.90 | 29.44 | 29.90 |
| Round robin test 01 | Salmonella spp. | 18.79 | 19.76 | 27.73 | 29.32 |
| Round robin test 02 | Salmonella spp. | 17.54 | 20.88 | 28.71 | 27.8 |
| Round robin test 03 | Salmonella spp. | 17.40 | 20.88 | 27.31 | 28.47 |
| Sesame | Salmonella spp. | 25.27 | 30.13 | 31.06 | 28.32 |
| Onion mettwurst sausage | Salmonella spp. | 32.00 | 30.56 | 29.32 | 30.23 |
| Dairy product | L. monocytogenes | no Ct | no Ct | 28.92 | 29.52 |
| Duck stripes | L. monocytogenes | 30.41 | 30.64 | 29.89 | 30.85 |
| Turkey breast | L. monocytogenes | 21.96 | 34.16 | 30.21 | 30.29 |
| Marinated duck | L. monocytogenes | 33.66 | 35.53 | 29.02 | 31.33 |
| Dairy product | Cronobacter spp. | 37.86 | 42.00 | 28.33 | 28.94 |
| Dairy product | Cronobacter spp. | 35.32 | 36.47 | 28.99 | 28.88 |
| Whole milk | Campylobacter spp. | 23.19 | 30.50 | 27.90 | 31.63 |
| Whole milk | Campylobacter spp. | 18.96 | 23.46 | 27.63 | 29.48 |
| Turkey | Campylobacter spp. | 17.33 | 19.10 | 28.02 | 29.03 |

The Ct values for the reference DNA ("inhibition control") confirm the quality of the extraction method, say that the RT-PCR reaction was not inhibited by DNA polymerase inhibitors from the extracted food matrix. A lowered Ct value in the test system would indicate that the sample was contaminated with pathogen. In essence, the CTAB method produced very similar results as the talc/salt protocol. The DNA prepared using the talc/salt protocol had generally a higher quality compared to the CTAB method with the only exception of "dark chocolate" which is rich in polyphenol and catechins. An optional extraction is however contemplated after the talc/PBS salt extraction prior DNA desalting. Notwithstanding, the talc/salt protocol proved fully satisfactory for this traditionally difficult food matrix.

The invention claimed is:

1. Composition for use in extracting and purifying nucleic acids from food samples characterized in that the composition is a mixture of solids comprising
   from 10 to 40 percent by weight particles consisting of water-insoluble hydrated magnesium silicate and having a median particle size from 0.8 to 2.5 μm, and
   from 20 to 70 percent by weight crystalline phosphate buffered saline which is readily water-soluble to produce a solution having a pH from 5.5 to 7.0 at 70 to 95 degrees Celsius.

2. Composition as claimed in claim 1, wherein the mixture of solids has been portioned as a tablet or capsule having a known predefined weight.

3. Composition as claimed in claim 1, further comprising from 20 to 35 percent by weight of a hydrophilic colloid effective to disperse the mixture of solids in water.

4. Composition as claimed in claim 1, comprising particles of hydrated magnesium silicate having a median particle size of from 1.0 to 2.0 μm.

5. Tablet or capsule essentially comprising a composition as claimed in claim 1, comprising
   from 10 to 25 percent by weight of water-insoluble hydrated magnesium silicate particles;
   from 45 to 70 percent by weight phosphate buffered saline, and
   from 20 to 30 percent by weight of a hydrophilic colloid effective to disperse the mixture of solids in water.

6. Composition according to claim 1, further comprising one or more non-chaotropic lysing agents.

7. Composition according to claim 3, wherein the hydrophilic colloid is a member of the group consisting of cellulose, carboxy-methyl cellulose, cellulose derivatives, alginate, starch, xantan gum, arabic gum, guar gum and mixtures thereof.

8. Method of isolating DNA from a diversity of feed and food samples, including beverages, for subsequent PCR analysis, comprising the following steps
   obtaining a predefined weight or volume amount of the sample, and transferring the sample into a vessel;
   adding a predefined amount of the mixture of solids as claimed in claim 1 to obtain a weight ratio of solids to sample in the vessel from 1:5 to 5.1;
   adding an amount of water to dissolve the buffer components of the mixture of solids to obtain an aqueous phosphate buffered saline solution having a pH from 5.5 to 7.0 and a salt concentration of 0.6 to 1.2 Mol/L,
   obtaining a solution or dispersion of the sample and the mixture of solids in phosphate buffered saline and heating the solution or dispersion up to a temperature from 70 to 95 degrees Celsius for 1 minute to 30 minutes to release the nucleic acids from the cellular materials and other water-insoluble components of the sample;
   separating the water-insoluble components of the sample and of the mixtures of solids from the aqueous phase together with the components adsorbed on the magnesium silicate particles of the mixture of solids;
   removal of an aqueous supernatent or filtrate containing soluble nucleic acids, followed by a desalting step to obtain a solution of the sample DNA suitable for PCR analysis.

9. Kit of parts for extracting and purifying nucleic acids from samples, comprising portioned amounts of the composition as claimed in claim 1.

10. Composition as claimed in claim 4, wherein said median particle size is from 1.2 to 1.5 μm.

11. Method as claimed in claim 8, wherein said sample comprises a member of the group consisting of small particles, a solution and a dispersion.

12. Method as claimed in claim 8, wherein said solution or dispersion is heated up to a temperature from 70 to 95 degrees Celsius for about 5 minutes to 20 minutes.

13. Method as claimed in claim 8, wherein said water-insoluble components are separated from the aqueous phase by centrifugation or filtration.

* * * * *